(12) United States Patent
Yoon et al.

(10) Patent No.: US 9,304,210 B2
(45) Date of Patent: Apr. 5, 2016

(54) X-RAY DETECTOR, METHOD FOR DRIVING THE SAME, AND X RAY PHOTOGRAPHING SYSTEM INCLUDING THE SAME

(71) Applicants: Kyung Hun Yoon, Yongin (KR); Man Seung Cho, Yongin (KR)

(72) Inventors: Kyung Hun Yoon, Yongin (KR); Man Seung Cho, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 185 days.

(21) Appl. No.: 13/921,274

(22) Filed: Jun. 19, 2013

(65) Prior Publication Data

US 2013/0343522 A1 Dec. 26, 2013

(30) Foreign Application Priority Data

Jun. 22, 2012 (KR) ........................ 10-2012-0067496

(51) Int. Cl.
| | | |
|---|---|---|
| *G01T 1/17* | (2006.01) | |
| *A61B 6/00* | (2006.01) | |
| *H04N 5/32* | (2006.01) | |
| *H04N 5/353* | (2011.01) | |
| *H04N 5/374* | (2011.01) | |
| *H04N 5/378* | (2011.01) | |

(52) U.S. Cl.
CPC ... *G01T 1/17* (2013.01); *A61B 6/42* (2013.01); *H04N 5/32* (2013.01); *A61B 6/4233* (2013.01); *H04N 5/353* (2013.01); *H04N 5/374* (2013.01); *H04N 5/378* (2013.01)

(58) Field of Classification Search
CPC ....... H04N 5/32; H04N 5/353; H04N 5/3597; H04N 5/374
See application file for complete search history.

(56) References Cited

U.S. PATENT DOCUMENTS

| | | |
|---|---|---|
| 5,887,049 A | 3/1999 | Fossum |
| 7,211,803 B1 | 5/2007 | Dhurjaty et al. |
| 2007/0145282 A1 | 6/2007 | Campbell |
| 2008/0179531 A1* | 7/2008 | Scheffer ................... 250/370.11 |

FOREIGN PATENT DOCUMENTS

KR 10-2010-0027808 A 3/2010

* cited by examiner

*Primary Examiner* — Hoon Song
(74) *Attorney, Agent, or Firm* — Lee & Morse, P.C.

(57) ABSTRACT

An X-ray detector includes a panel including a plurality of photo-sensing pixels, the photo-sensing pixels being configured to detect an X-ray and to perform photoelectric conversion to output electrical signals, and a read-out integrated circuit connected to the panel, the read-out integrated circuit being configured to read out the electrical signals from the photo-sensing pixels and to generate a self-triggering signal based on the read-out electrical signals.

23 Claims, 7 Drawing Sheets

X-RAY DETECTOR, METHOD FOR DRIVING THE SAME, AND X RAY PHOTOGRAPHING SYSTEM INCLUDING THE SAME

CROSS-REFERENCE TO RELATED APPLICATION

This application claims priority from Korean Patent Application No. 10-2012-0067496 filed on Jun. 22, 2012, in the Korean Intellectual Property Office, and all the benefits accruing therefrom under 35 U.S.C. 119, the contents of which in its entirety are herein incorporated by reference.

BACKGROUND

1. Field

The present inventive concept relates to an X-ray detector, an X-ray photographing system including the X-ray detector, and a method for driving the X-ray detector. More particularly, the present inventive concept relates to an X-ray detector capable of self-triggering the X-ray detector, an X-ray photographing system including the X-ray detector, and a method for driving the X-ray detector.

2. Description of the Related Art

An X-ray photographing system is a system which transmits an X-ray through an object, e.g., a human body, and detects the amount of transmitted X-ray to photograph the object's internal structure. The X-ray photographing system is generally used as, e.g., a medical inspection system, non-destructive inspection system, or the like.

In a conventional X-ray photographing system, an image is photographed by using a film, a computed radiography (CR) method, a digital radiography (DR) method, or the like. In case of the DR type X-ray photographing system, as opposed to using a film or CR method, there is a need for a process of triggering the X-ray detector through signal exchange with the X-ray detector before the X-ray is generated from an X-ray source.

SUMMARY

Example embodiments provide an X-ray detector capable of self-triggering the X-ray detector, without connecting an X-ray source and the X-ray detector, an X-ray photographing system including the X-ray detector, and a method for driving the X-ray detector.

Example embodiments also provide an X-ray detector capable of self-triggering the X-ray detector, based on the X-ray incident onto the X-ray detector without using a separate device for triggering, an X-ray photographing system including the X-ray detector, and a method for driving the X-ray detector Example embodiments may be directed toward an X-ray detector that includes a panel including a plurality of photo-sensing pixels, the photo-sensing pixels being configured to detect an X-ray and to perform photoelectric conversion to output electrical signals, and a read-out integrated circuit connected to the panel, the read-out integrated circuit being configured to read out the electrical signals from the photo-sensing pixels and to generate a self-triggering signal based on the read-out electrical signals.

The read-out integrated circuit may include a read-out unit configured to read out the electrical signals from the photo-sensing pixels, and a triggering signal generating unit configured to generate the self-triggering signal based on signals output from the read-out unit.

The X triggering signal generating unit may be configured to generate the self-triggering signal if the signals output from the read-out unit are equal to or greater than a threshold value.

The read-out unit may include an amplifier, a capacitor, and a reset switch, wherein the amplifier includes an input terminal to receive the electrical signals from the photo-sensing pixels, wherein a first terminal of the capacitor is connected to the input terminal, and a second terminal of the capacitor is connected to an output terminal of the amplifier, and wherein the reset switch is connected in parallel with the capacitor.

The reset switch may be closed during a first time period, and is open during a second time period, the first time period and the second time period being alternately repeated.

The triggering signal generating unit may be configured to generate the self-triggering signal if an output signal from the amplifier during the first time period is equal to or greater than a threshold value.

The X-ray detector may further include a gate driver configured to provide gate signals to the photo-sensing pixels.

The self-triggering signal may stop an operation of the gate driver, and switches a mode of the X-ray detector to an integration mode.

Example embodiments may also be directed toward an X-ray detector that includes a panel including a plurality of photo-sensing pixels arranged in a matrix, the photo-sensing pixels being configured to detect an X-ray and to perform photoelectric conversion to output electrical signals, a gate driver configured to provide gate signals to the photo-sensing pixels, and a read-out integrated circuit including a read-out unit and a triggering signal generating unit, the read-out unit being configured to read out the electrical signals from the photo-sensing pixels, and the triggering signal generating unit being configured to generate a self-triggering signal based on electrical signals output by the read-out unit.

The read-out unit may include an amplifier, a capacitor, and a reset switch, wherein the amplifier includes an input terminal to receive the electrical signals from the photo-sensing pixels, wherein a first terminal of the capacitor is connected to the input terminal, and a second terminal of the capacitor is connected to an output terminal of the amplifier, and wherein the reset switch is connected in parallel with the capacitor.

The reset switch may be closed during a first time period and open during a second time period, the first time period and the second time period being alternately repeated.

The triggering signal generating unit may be configured to generate the self-triggering signal if an output signal from the amplifier during the first time period is equal to or greater than a threshold value.

The read-out unit may sequentially read out the photo-sensing pixels arranged in the matrix on a column basis every repeated first time period.

The self-triggering signal may stop an operation of the gate driver, and switches a mode of the X-ray detector to an integration mode.

Example embodiments may also be directed toward an X-ray photographing system that includes an X-ray source configured to generate an X-ray, and an X-ray detector configured to detect the X-ray generated by the X-ray source, the X-ray detector having a panel including a plurality of photo-sensing pixels, the photo-sensing pixels being configured to detect an X-ray and to perform photoelectric conversion to output electrical signals, and a read-out integrated circuit connected to the panel, the read-out integrated circuit being configured to read out the electrical signals from the photo-sensing pixels and to generate a self-triggering signal based on the read-out electrical signals.

The X-ray photographing system may further include a control unit configured to control an operation of the X-ray source and to process signals output from the X-ray detector.

The read-out integrated circuit may include a read-out unit configured to read out the electrical signals from the photo-sensing pixels, and a triggering signal generating unit configured to generate the self-triggering signal based on output signals from the read-out unit.

The triggering signal generating unit may be configured to generate the self-triggering signal if the output signals from the read-out unit are equal to or greater than a threshold value.

The X-ray photographing system may further include a memory configured to store signals output by the X-ray detector, the memory being configured to store an image before or after the self-triggering signal is generated.

Example embodiments may also be directed toward a method for driving an X-ray detector with a panel including a plurality of photo-sensing pixels which detect an X-ray and perform photoelectric conversion to output electrical signals, and a read-out integrated circuit which reads out the electrical signals from the photo-sensing pixels, the method including reading out the electrical signals from the photo-sensing pixels during a first time period and resetting the photo-sensing pixels, the reading out and resetting including generating a self-triggering signal based on the read-out electrical signals, and charging the electrical signals from the photo-sensing pixels during a second time period.

Operation modes of the X-ray detector may include a sleep mode, a standby mode, and an integration mode, wherein the standby mode includes the first time period and the second time period, and wherein generating a self-triggering signal includes switching a mode of the X-ray detector to the integration mode.

In the standby mode, the first time period and the second time period may be alternately repeated.

Generating the self-triggering signal may include generating a self-triggering signal if output signals from the read-out unit are equal to or greater than a threshold value.

BRIEF DESCRIPTION OF THE DRAWINGS

The above and other aspects and features will become more apparent by describing in detail exemplary embodiments thereof with reference to the attached drawings, in which.

DETAILED DESCRIPTION

Example embodiments will now be described more fully hereinafter with reference to the accompanying drawings, in which preferred embodiments are shown. Embodiments may, however, be embodied in different forms and should not be construed as limited to the embodiments set forth herein. Rather, these embodiments are provided so that this disclosure will be thorough and complete, and will fully convey the scope of the invention to those skilled in the art. The same reference numbers indicate the same components throughout the specification. In the attached figures, the thickness of layers and regions is exaggerated for clarity.

It will also be understood that when a layer is referred to as being "on" another layer or substrate, it can be directly on the other layer or substrate, or intervening layers may also be present. In contrast, when an element is referred to as being "directly on" another element, there are no intervening elements present.

Hereinafter, embodiments will be described in detail with reference to the accompanying drawings.

Figure 1:
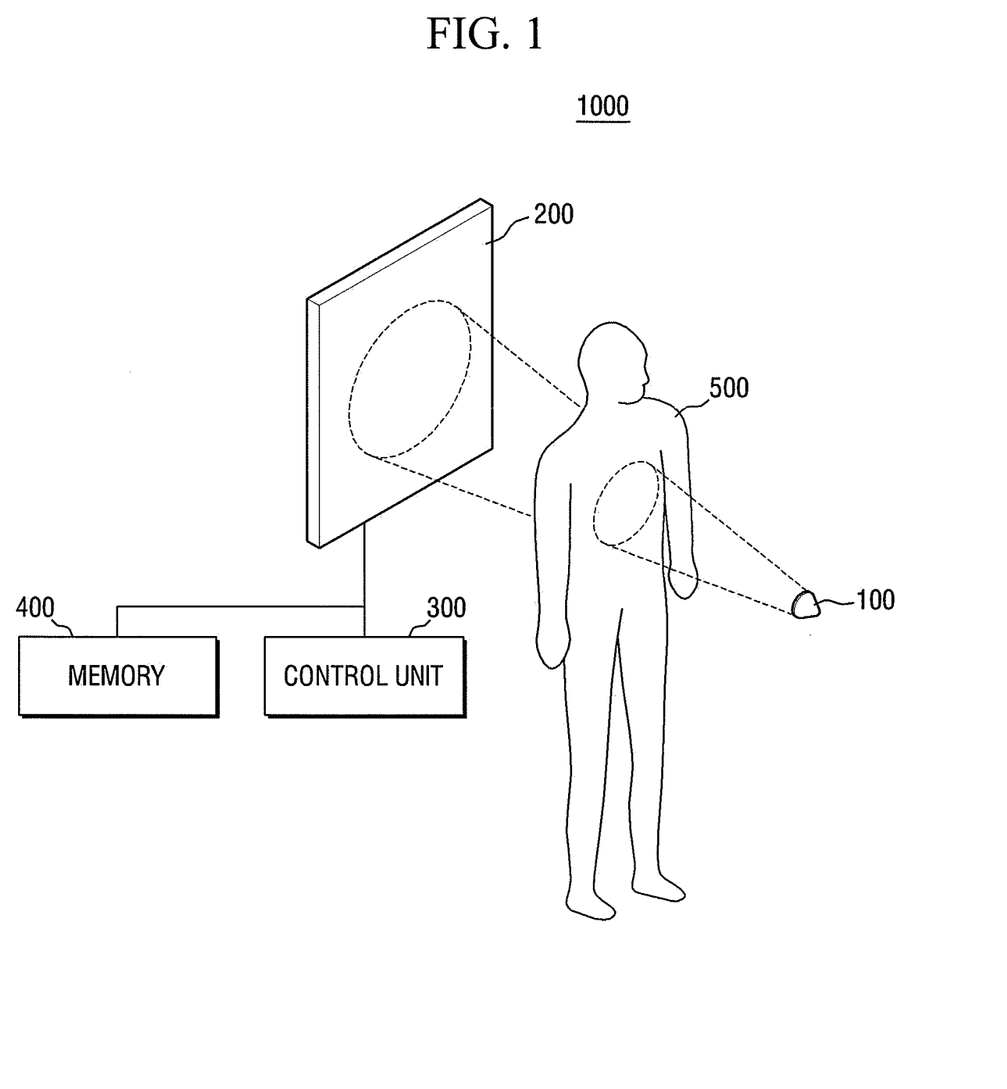
FIG. 1 is a conceptual diagram of an X-ray photographing system in accordance with an embodiment.

FIG. 1 is a conceptual diagram of an X-ray photographing system in accordance with an embodiment. Referring to FIG. 1, an X-ray photographing system 1000 includes an X-ray source 100 and an X-ray detector 200.

The X-ray source 100 is an X-ray generating unit which generates an X-ray to be incident onto a specific region (i.e., a region to be inspected) of a subject 500.

The X-ray detector 200 is a unit which detects the X-ray generated from the X-ray source 100. For example, after the X-ray source 100 generates and emits an X-ray toward the specific region of the subject 500, the X-ray detector 200 detects the X-ray that penetrates through the subject 500. The X-ray detector 200 will be described in detail later.

The X-ray photographing system 1000 may include a control unit 300. The control unit 300 may communicate with the X-ray source 100 and the X-ray detector 200 to control the X-ray source 100 and the X-ray detector 200. Although a case where the control unit 300 performs wired communication with the X-ray detector 200 and performs wireless communication with the X-ray source 100 has been illustrated in FIG. 1, embodiments are not limited thereto. For example, the control unit 300 may receive an output from the X-ray detector 200 and convert electrical signals into image signals. The image signals generated from the control unit 300 may be displayed on a separate display device (not shown).

The X-ray source 100 may include a memory 400. The memory 400 may store the electrical signals which are output signals from the X-ray detector 200, and store the image signals generated from the control unit 300. The electrical signals or image signals stored in the memory 400 may be used in an image correction operation, e.g., offset correction. For example, the memory 400 may store a current image, and a previous or next image, and the control unit 300 or the like may perform offset correction, e.g., of the current image, based on the images stored in the memory 400, e.g., based on the previous image. Here, the current image may mean an image stored while the X-ray detector 200 operates in an integration mode when a self-triggering signal is generated.

Figure 2:
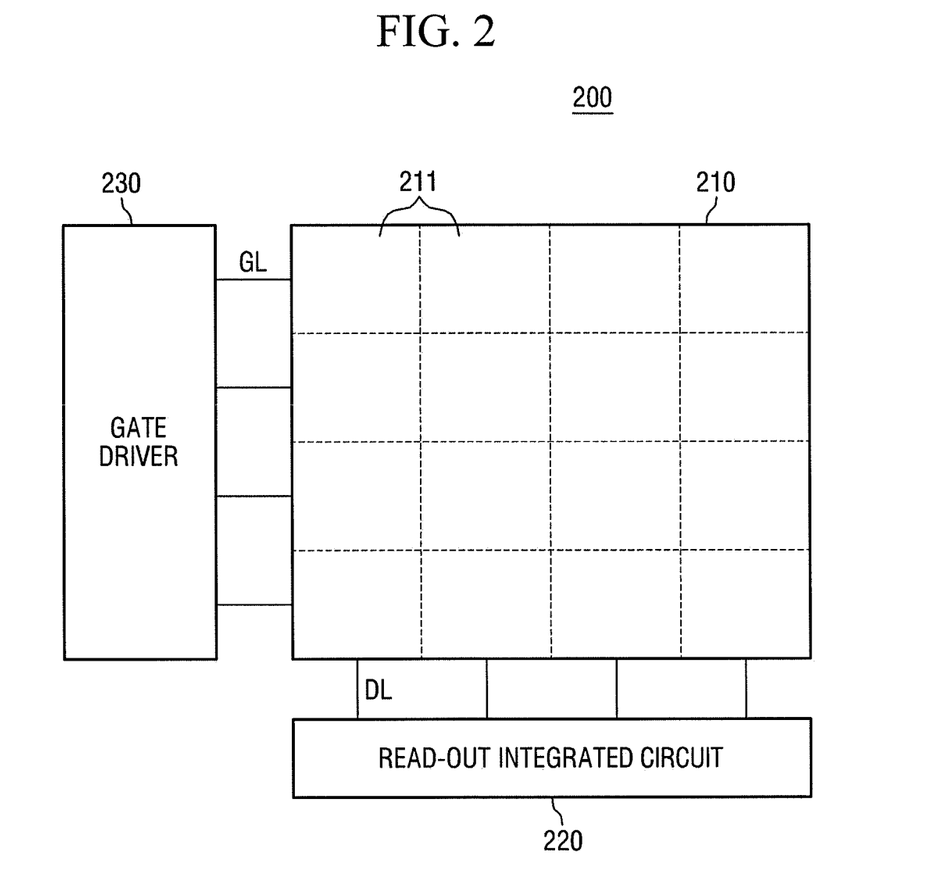
FIG. 2 is a conceptual diagram of an X-ray detector in accordance with an embodiment.

Hereinafter, the X-ray detector 200 will be described in detail with reference to FIG. 2. FIG. 2 is a conceptual diagram of the X-ray detector 200.

Referring to FIG. 2, the X-ray detector 200 includes a panel 210 and a read-out integrated circuit 220. In some embodiments, the X-ray detector 200 may include a gate driver 230.

The panel 210 includes a plurality of photo-sensing pixels 211 which detect the X-ray generated from the X-ray source 100 and perform photoelectric conversion to output electrical signals corresponding to the information detected by the photo-sensing pixels 211, e.g., amount of detected X-ray. The photo-sensing pixels 211 may be arranged in a matrix on the panel 210. For convenience of explanation, a case where the photo-sensing pixels 211 are arranged in a 4×4 matrix has been illustrated in FIG. 2, but embodiments are not limited thereto, i.e., the number of the photo-sensing pixels 211 and the shape of the matrix of the photo-sensing pixels 211 may be variously set. The panel 210 and the photo-sensing pixels 211 included in the panel 210 are described in more detail below with reference to FIG. 3.

Figure 3:
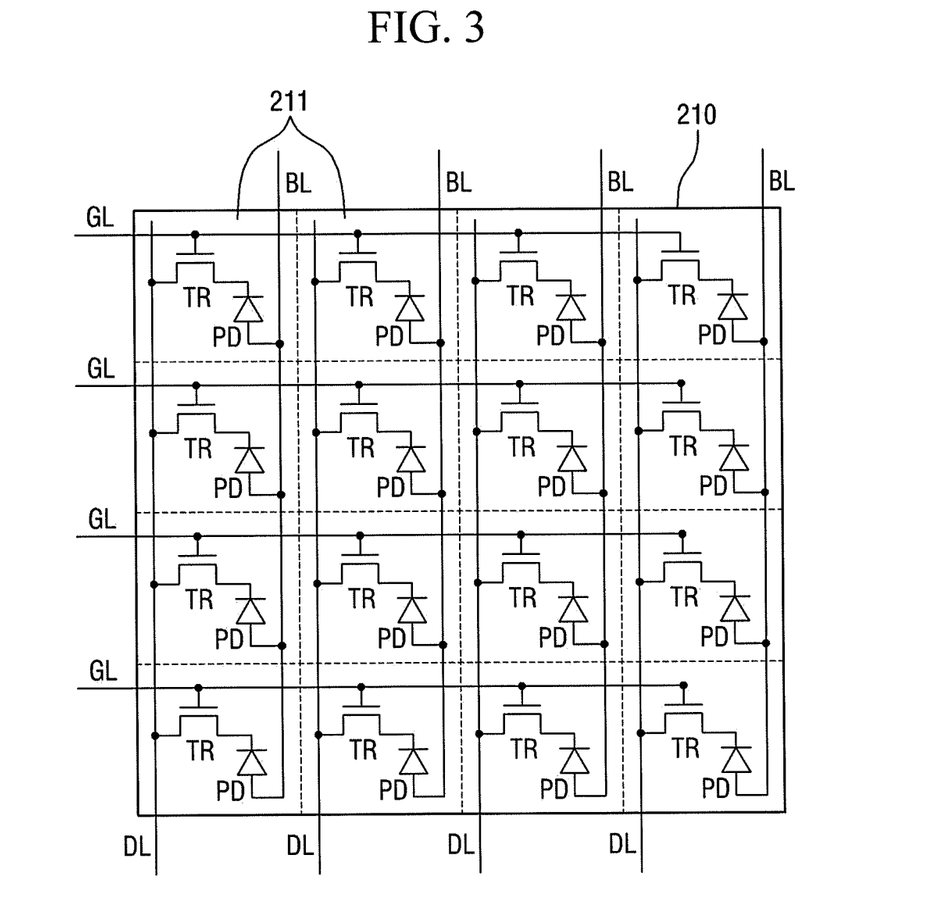
FIG. 3 is a conceptual diagram of a panel of the X-ray detector in accordance with an embodiment.

FIG. 3 is a conceptual diagram of the panel 210 of the X-ray detector 200 in accordance with an embodiment. Referring to FIG. 3, the panel 210 includes a plurality of the photo-sensing pixels 211 which are arranged in a matrix pattern in regions, e.g., vicinity, of intersections of gate lines GL and data lines DL. The gate lines GL and the data lines DL are substantially arranged to be perpendicular to each other.

Each of the photo-sensing pixels 211 may include a photodiode PD, i.e., which detects the X-ray from the X-ray source 100 to output a photodetection voltage, and a transistor TR, i.e., which transmits the electrical signal, e.g., photodiode voltage, output from the photodiode PD.

The photodiode PD is an element, e.g., a PIN diode, which converts incident light into an electrical signal by a photoelectric effect. First electrodes of the photodiodes PD may be electrically connected to first electrodes of the transistors TR, and second electrodes of the photodiodes PD may be electrically connected to bias lines BL to which a bias voltage is applied.

Although not shown in FIGS. 2 and 3, the panel 210 may include a bias driver. The bias driver may apply a drive voltage through a plurality of the bias lines BL. For example, the bias driver may selectively apply a reverse bias or forward bias to the photodiodes PD.

The transistor TR is a switching element which transmits the photodetection voltage, i.e., the electrical signal output from the photodiode PD. Gate electrodes of the transistors TR may be electrically connected to the gate lines GL, and second electrodes of the transistors TR may be electrically connected to the read-out integrated circuit 220 through the data lines DL.

The gate driver 230 may provide gate signals to the photo-sensing pixels 211. The gate driver 230 may sequentially apply gate pulses having a gate-on voltage level to the transistors TR through the gate lines GL, and the transistors TR may be turned on in response to the gate pulses. When the transistors TR are turned on, the electrical signals output from the photodiodes PD may be transmitted to the read-out integrated circuit 220 through the transistors TR and the data lines DL.

Referring again to FIG. 2, the read-out integrated circuit 220 may read out the electrical signals from the photo-sensing pixels 211, i.e., from the turned-on transistors TR of corresponding photo-sensing pixels 211. The read-out integrated circuit 220 may generate a self-triggering signal for the X-ray detector 200 based on the electrical signals received from the turned on transistors TR. The read-out integrated circuit 220 is described in more detail below with reference to FIGS. 4 and 5.

Figure 4:
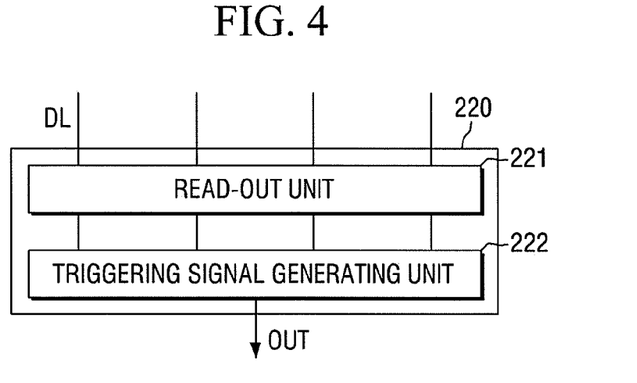
FIGS. 4 and 5 are conceptual diagrams of a read-out integrated circuit (IC) of the X-ray detector in accordance with an embodiment.
Figure 5:
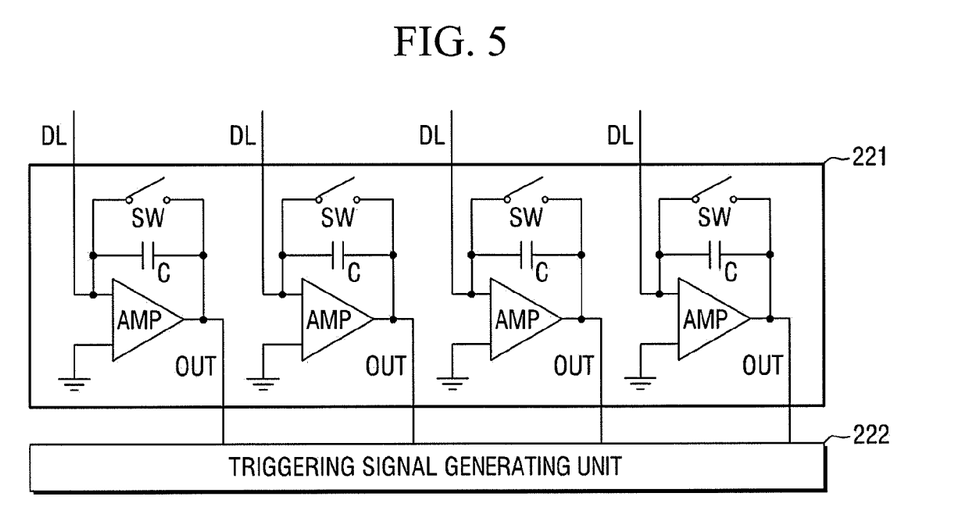

FIGS. 4 and 5 are conceptual diagrams of the read-out integrated circuit 220 of the X-ray detector 100 in accordance with an embodiment.

Referring to FIG. 4, the read-out integrated circuit 220 includes a read-out unit 221 and a triggering signal generating unit 222. The read-out unit 221 may read out the electrical signals from the photo-sensing pixels 211.

Referring to FIG. 5, the read-out unit 221 may include one or more amplifiers AMP, one or more capacitors C, and one or more reset switches SW. In some embodiments, the number of the amplifiers AMP, the number of the capacitors C, and the number of the reset switches SW may be the same as the number of the data lines DL.

The amplifiers AMP may include input terminals to receive the electrical signals from the photo-sensing pixels 211. The amplifiers AMP may include first input terminals which are connected to the data lines DL transmitting the electrical signals from the photo-sensing pixels 211, second input terminals to which a reference voltage, e.g., a ground voltage, is input, and output terminals for output signals. In some embodiments, the first input terminals and the second input terminals may be inverting input terminals and non-inverting input terminals, respectively. The output signals from the output terminals of the amplifiers AMP may be transmitted to the triggering signal generating unit 222. Although not shown in FIGS. 4 and 5, the read-out unit 221 may further include a multiplexer, and the multiplexer may sequentially output the output signals from the amplifiers AMP to the control unit 300 or the like.

One-side terminals of the capacitors C may be connected to the first input terminals of the amplifiers AMP, and the other-side terminals of the capacitors C may be connected to the output terminals of the amplifiers AMP.

Each of the reset switches SW may be connected in parallel with each of the capacitors C. The reset switch SW may discharge the voltage charged in the capacitor C to reset the capacitor C. One terminal of the reset switch SW may be electrically connected to the one-side terminal of the capacitor C, and the other terminal of the reset switch SW may be electrically connected to the other-side terminal of the capacitor C. Accordingly, when the reset switch SW is open, voltage may be charged between both terminals of the capacitor C, whereas when the reset switch SW is closed, both terminals of the capacitor C may be electrically connected to discharge the voltage charged between both terminals of the capacitor C.

The triggering signal generating unit 222 may generate a self-triggering signal based on the output signals from the read-out unit 221. A method for driving the X-ray detector 200, i.e., the generation of the self-triggering signal by the triggering signal generating unit 222, will be described in detail with reference to FIGS. 6 to 8.

Figure 6:
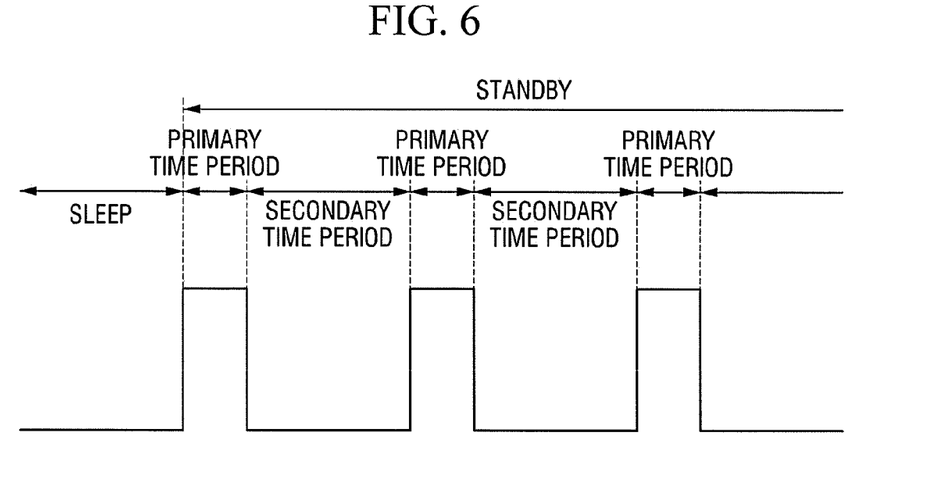
FIGS. 6 to 8 are graphs for explaining a method for driving the X-ray detector in accordance with various embodiments.
Figure 7:
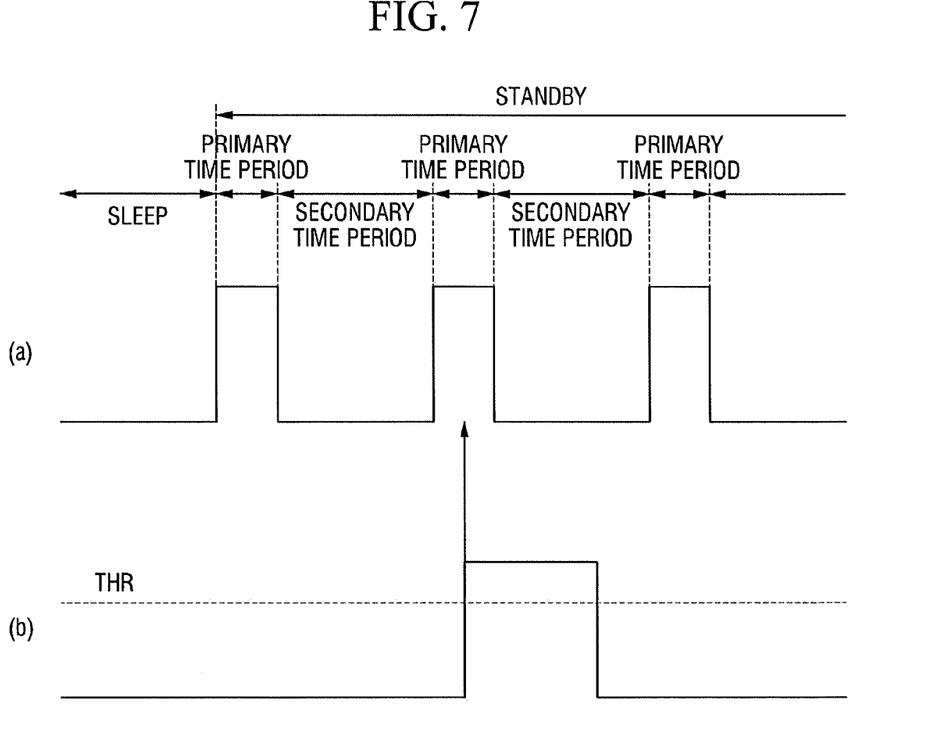
Figure 8:
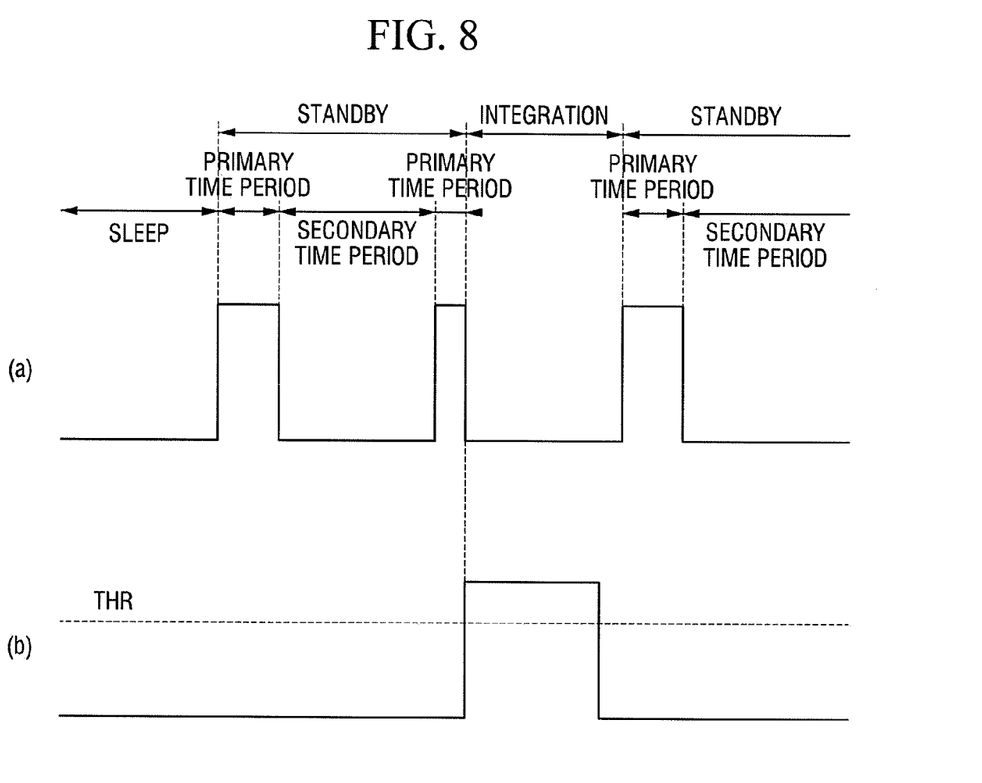

FIGS. 6 to 8 are graphs for explaining a method for driving the X-ray detector 200 in accordance with various embodiments.

FIG. 6 is a graph for explaining a general operation mode of the X-ray detector 200. The X-ray detector 200 may operate in any one of a sleep mode, a standby mode, and an integration mode.

For example, referring to FIG. 6, the X-ray detector 200 may initially operate in the sleep mode. If a signal for X-ray inspection is generated while the X-ray detector 200 operates in the sleep mode, the X-ray detector 200 switches to the standby mode. For example, the signal for X-ray inspection may be a photographing signal for a new subject 500, e.g., may mean that a new patient enters an X-ray photographing room.

Referring to FIG. 6, the standby mode may include a first time period, i.e., primary period, and a second time period, i.e., secondary period. The first time period and the second time period may be alternately repeated in the standby mode.

During the first time period, the read-out integrated circuit 220 of the X-ray detector 200 may read out the electrical signals from the photo-sensing pixels 211 and reset the photo-sensing pixels 211. That is, during the first time period, the read-out unit 221 of the read-out integrated circuit 220 may read out the electrical signals from the photo-sensing pixels 211, and may reset the photo-sensing pixels 211 by closing the reset switches SW of the read-out unit 221 to discharge the voltage charged in the capacitors C.

During the second time period, the read-out integrated circuit 220 of the X-ray detector 200 may charge the electrical signals from the photo-sensing pixels 211. That is, during the second time period, the read-out unit 221 of the read-out integrated circuit 220 may charge the electrical signals from the photo-sensing pixels 211, i.e., the photodetection voltage, in the capacitors C. In some embodiments, the second time period may be set to be equal to or longer than the X-ray irradiation time of the X-ray source 100.

The read-out unit 221 may sequentially read out the photo-sensing pixels 211 arranged in a matrix on a column basis every first time period. For example, referring to FIG. 3, the read-out unit 221 may read out the photo-sensing pixels 211 in a leftmost column among the photo-sensing pixels 211 arranged in the 4×4 matrix of FIG. 3 during a first first time period, read out the photo-sensing pixels 211 in the second column from the left among the photo-sensing pixels 211 arranged in the 4×4 matrix of FIG. 3 during a second first time period, and read out the photo-sensing pixels 211 in the third column from the left among the photo-sensing pixels 211 arranged in the 4×4 matrix of FIG. 3 during a third first time period.

FIG. 7 illustrates detection of electrical signals in different time periods of the X-ray detector 200. That is, FIG. 7(a) is the graph of the operation mode of the X-ray detector 200 as shown in FIG. 6, and FIG. 7 (b) is a graph showing the magnitudes of the electrical signals read out by the read-out unit 221.

The X-ray detector 200 begins to operate in the standby mode, and during the first time period, the read-out unit 221 may read out the electrical signals from the photo-sensing pixels 211. The triggering signal generating unit 222 may generate the self-triggering signal based on the electrical signals output from the read-out unit 221. For example, the triggering signal generating unit 222 may generate the self-triggering signal if the output signals from the read-out unit 221 are equal to or greater than a threshold value THR.

That is, referring to FIG. 7, if output signals equal to or greater than the threshold value THR are not detected during the first first time period, no self-triggering signal is generated in the first first time period. However, if output signals equal to or greater than the threshold value THR are detected during the second first time period (see signal in FIG. 7(b)), the self-triggering signal may be generated in the second first time period.

FIG. 8 illustrates when output signals equal to or greater than the threshold value THR are detected. That is, FIG. 8 (b) is a graph showing the magnitudes of the electrical signals read out by the read-out unit 221, and FIG. 8 (a) is a graph for explaining the operation mode of the X-ray detector when the output signals equal to or greater than the threshold value THR are detected.

As described above, if output signals equal to or greater than the threshold value THR are not detected during the first first time period but detected during the second first time period, the self-triggering signal may be generated in the second first time period (FIG. 8(b)). When the self-triggering signal is generated, i.e., when it is determined that the X-ray is incident onto the X-ray detector 200, operations of the gate driver 230, i.e., which is performed in sequence, are stopped, i.e., so operation corresponding to the first time period is stopped, and the mode of the X-ray detector 200 is switched to the integration mode. In other words, once the self-triggering signal is generated, i.e., during the time that X-ray is incident onto the X-ray detector 200, the X-ray detector 200 operates in the integration mode, and when the integration mode is completed, i.e., when the X-ray stops being incident onto the X-ray detector 200, the X-ray detector 200 switches back the standby mode again.

In case of a DR type X-ray photographing system, there is a need for a process for triggering the X-ray detector through signal exchange with the X-ray detector before the X-ray is generated from the X-ray source. In the X-ray photographing system according to example embodiments, without a separate device for triggering or exchanging signals between the X-ray source and the X-ray detector, it is possible to detect whether the X-ray is incident on the X-ray detector 200 in real time by the output of the read-out unit 221 of the X-ray detector 200, to generate the self-triggering signal based on the electrical signals of the read-out unit 221, and to store an image by switching the mode of the D-ray detector 200 to the integration mode.

Figure 9:
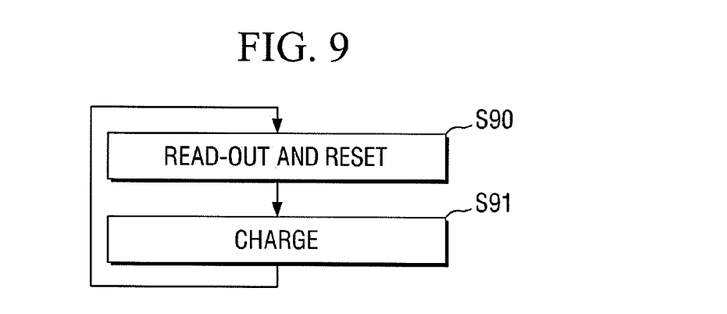
FIG. 9 is a flowchart showing a method for driving the X-ray detector in accordance with an embodiment.

FIG. 9 is a flowchart showing a method for driving an X-ray detector in accordance with an embodiment.

First, during the first time period, the electrical signals from the photo-sensing pixels of the X-ray detector are read out, and the photo-sensing pixels are reset (S90). Since the operations of reading out the electrical signals from the photo-sensing pixels and resetting the photo-sensing pixels are substantially the same as the operations of reading out the electrical signals from the photo-sensing pixels and resetting the photo-sensing pixels as illustrated in FIGS. 1 to 8, a repeated description will be omitted.

In some embodiments, the operations of reading out the electrical signals from the photo-sensing pixels and resetting the photo-sensing pixels may include generating the self-triggering signal based on the read-out electrical signals. Since the operation of generating the self-triggering signal is substantially the same as the operation of generating the self-triggering signal as illustrated in FIGS. 1 to 8, a repeated description will be omitted.

Then, during the second time period, the electrical signals from the photo-sensing pixels are charged (S91). Since the operation of charging the electrical signals from the photo-sensing pixels is substantially the same as the operation of charging the electrical signals from the photo-sensing pixels as illustrated in FIGS. 1 to 8, a repeated description will be omitted.

Figure 10:
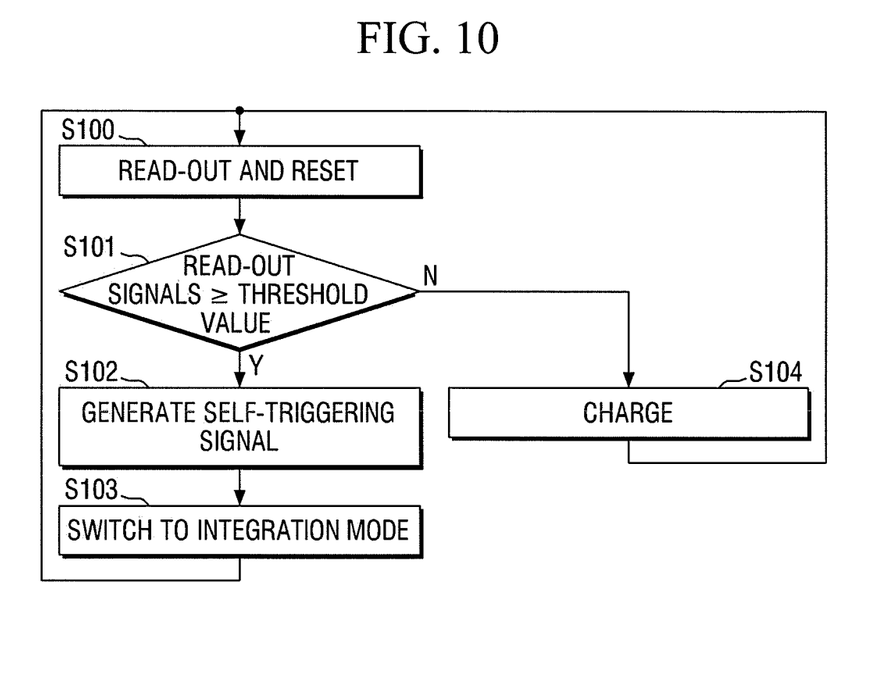
FIG. 10 is a flowchart showing a method for driving the X-ray detector in accordance with another embodiment.

FIG. 10 is a flowchart showing a method for driving the X-ray detector in accordance with another embodiment.

First, during the first time period, the electrical signals from the photo-sensing pixels of the X-ray detector are read out, and the photo-sensing pixels are reset (S100). Since the operations of reading out the electrical signals from the photo-sensing pixels and resetting the photo-sensing pixels are substantially the same as the operations of reading out the electrical signals from the photo-sensing pixels and resetting the photo-sensing pixels as discussed with reference to FIG. 9, a repeated description will be omitted.

Then, during the first time period, the read-out integrated circuit of the X-ray detector determines whether the output signals from the read-out unit are equal to or greater than the threshold value (S101). If the output signals from the read-out unit are not equal to or greater than the threshold value, it proceeds to the second time period, and the electrical signals from the photo-sensing pixels are charged (S104). Since the operation of charging the electrical signals from the photo-sensing pixels is substantially the same as the operation of charging the electrical signals from the photo-sensing pixels as illustrated in FIG. 9, a repeated description will be omitted.

Further, if the output signals from the read-out unit are equal to or greater than the threshold value, the X-ray detector generates the self-triggering signal (S102), and the X-ray detector switches the mode to the integration mode (S103). Since the operations of generating the self-triggering signal and switching the mode of the X-ray detector to the integration mode are substantially the same as the operations of generating the self-triggering signal and switching the mode of the X-ray detector to the integration mode as illustrated in FIGS. 1 to 8, a repeated description will be omitted.

According to embodiments, at least the following effects can be obtained. It is possible to provide an X-ray detector capable of self-triggering the X-ray detector, i.e., start detection operation in integration mode, without connecting the X-ray source and the X-ray detector. Also, it is possible to provide an X-ray detector capable of self-triggering the X-ray detector based on the X-ray incident onto the X-ray detector, without using a separate device for the triggering. Further, an X-ray photographing system including the X-ray detector and a method for driving the X-ray detector are provided.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. An X-ray detector, comprising:
   a panel including a plurality of photo-sensing pixels, the photo-sensing pixels to receive an X-ray and to perform photoelectric conversion on the received X-ray to output electrical signals; and
   a read-out integrated circuit connected to the panel, the read-out integrated circuit to monitor whether the photo-sensing pixels receive the X-ray or not in a standby mode and to generate a self-triggering signal based on the electrical signals from the photo-sensing pixels, the self-triggering signal indicating that the photo-sensing pixels receive the X-ray, wherein
   the standby mode includes a first time period and a second time period, and wherein:
   during the second time period, the read-out integrated circuit charges the electrical signals, and
   during the first time period, the read-out integrated circuit reads out the electrical signals and resets the photo-sensing pixels by discharging the charged electrical signals, and wherein
   the second time period is equal to or longer than an irradiation time of the X-ray.

2. The X-ray detector of claim 1, wherein the read-out integrated circuit includes:
   a read-out circuit to read out the electrical signals from the photo-sensing pixels; and
   a triggering signal generator to generate the self-triggering signal based on signals output from the read-out circuit.

3. The X-ray detector of claim 2, wherein the triggering signal generator generates the self-triggering signal when the signals output from the read-out circuit are equal to or greater than a threshold value.

4. The X-ray detector of claim 2, wherein the read-out circuit includes an amplifier, a capacitor, and a reset switch, wherein the amplifier includes an input terminal to receive the electrical signals from the photo-sensing pixels, wherein a first terminal of the capacitor is connected to the input terminal and a second terminal of the capacitor is connected to an output terminal of the amplifier, and wherein the reset switch is connected in parallel with the capacitor, wherein:
   during the second time period, the capacitor charges the electrical signals, and
   during the first time period, the reset switch discharges the charged electrical signal in the capacitor.

5. The X-ray detector of claim 4, wherein the reset switch is closed during the first time period and is open during a second time period, the first time period and the second time period being alternately repeated.

6. The X-ray detector of claim 5, wherein the triggering signal generator generates the self-triggering signal when an output signal from the amplifier during the first time period is equal to or greater than a threshold value.

7. The X-ray detector of claim 1, further comprising:
   a gate driver to provide gate signals to the photo-sensing pixels.

8. The X-ray detector of claim 7, wherein the self-triggering signal stops an operation of the gate driver, and switches a mode of the X-ray detector to an integration mode.

9. An X-ray detector, comprising:
   a panel including a plurality of photo-sensing pixels arranged in a matrix, the photo-sensing pixels to receive an X-ray and to perform photoelectric conversion on the received X-ray to output electrical signals;
   a gate driver to provide gate signals to the photo-sensing pixels; and
   a read-out integrated circuit including a read-out circuit and a triggering signal generator, the read-out circuit to monitor whether the photo-sensing pixels receive the X-ray or not in a standby mode, and the triggering signal generator to generate a self-triggering signal based on electrical signals output by the read-out circuit, the self-triggering signal indicating that the photo-sensing pixels receive the X-ray, wherein
   the standby mode includes a first time period and a second time period, and wherein:
   during the second time period, the read-out integrated circuit charges the electrical signals, and
   during the first time period, the read-out integrated circuit reads out the electrical signals and resets the photo-sensing pixels by discharging the charged electrical signals, and wherein
   the second time period is equal to or longer than an irradiation time of the X-ray.

10. The X-ray detector of claim 9, wherein the read-out circuit includes an amplifier, a capacitor, and a reset switch, wherein the amplifier includes an input terminal to receive the electrical signals from the photo-sensing pixels, wherein a first terminal of the capacitor is connected to the input terminal and a second terminal of the capacitor is connected to an output terminal of the amplifier, and wherein the reset switch is connected in parallel with the capacitor, wherein:
    during the second time period, the capacitor charges the electrical signals, and
    during the first time period, the reset switch discharges the charged electrical signal in the capacitor.

11. The X-ray detector of claim 10, wherein the reset switch is closed during the first time period and is open during a second time period, the first time period and the second time period being alternately repeated.

12. The X-ray detector of claim 11, wherein the triggering signal generator generates the self-triggering signal when an output signal from the amplifier during the first time period is equal to or greater than a threshold value.

13. The X-ray detector of claim 11, wherein the read-out circuit sequentially reads out the photo-sensing pixels arranged in the matrix on a column basis every repeated first time period.

14. The X-ray detector of claim 9, wherein the self-triggering signal stops an operation of the gate driver, and switches a mode of the X-ray detector to an integration mode.

15. An X-ray photographing system, comprising:
an X-ray source to generate an X-ray; and
an X-ray detector to detect receive the X-ray generated by the X-ray source, the X-ray detector including:
a panel including a plurality of photo-sensing pixels, the photo-sensing pixels to perform photoelectric conversion on the received X-ray to output electrical signals, and
a read-out integrated circuit connected to the panel, the read-out integrated circuit to monitor whether the photo-sensing pixels receive the X-ray or not in a standby mode and to generate a self-triggering signal based on the electrical signals, the self-triggering signal indicating that the photo-sensing pixels receive the X-ray, wherein
the standby mode includes a first time period and a second time period, and wherein:
during the second time period, the read-out integrated circuit charges the electrical signals, and
during the first time period, the read-out integrated circuit reads out the electrical signals and resets the photo-sensing pixels by discharging the charged electrical signals, and wherein
the second time period is equal to or longer than an irradiation time of the X-ray.

16. The X-ray photographing system of claim 15, further comprising a controller to control an operation of the X-ray source and to process signals output from the X-ray detector.

17. The X-ray photographing system of claim 15, wherein the read-out integrated circuit includes:
a read-out circuit to read out the electrical signals from the photo-sensing pixels; and
a triggering signal generator to generate the self-triggering signal based on output signals from the read-out circuit.

18. The X-ray photographing system of claim 17, wherein the triggering signal generator generates the self-triggering signal when the output signals from the read-out circuit are equal to or greater than a threshold value.

19. The X-ray photographing system of claim 15, further comprising a memory to store signals output by the X-ray detector, the memory to store an image before or after the self-triggering signal is generated.

20. A method for driving an X-ray detector with a panel including a plurality of photo-sensing pixels which receive an X-ray and perform photoelectric conversion on the received X-ray to output electrical signals, and a read-out integrated circuit which monitors whether the photo-sensing pixels receive the X-ray or not in a standby mode, the method comprising:
reading out the electrical signals from the photo-sensing pixels and resetting the photo-sensing pixels during a first time period of the standby mode and
charging the electrical signals from the photo-sensing pixels during a second time period of the standby mode; and
generating a self-triggering signal based on the electrical signals, the self-triggering signal indicating that the photo-sensing pixels receive the X-ray, wherein
the second time period is equal to or longer than an irradiation time of the X-ray.

21. The method of claim 20, wherein operation modes of the X-ray detector includes a sleep mode, the standby mode, and an integration mode, and wherein generating the self-triggering signal includes switching a mode of the X-ray detector from the standby mode to the integration mode.

22. The method of claim 21, wherein in the standby mode, the first time period and the second time period are alternately repeated.

23. The method of claim 20, wherein the self-triggering signal is generated when output signals from the read-out unit are equal to or greater than a threshold value.

* * * * *